United States Patent [19]

Stetter et al.

[11] Patent Number: 4,614,534
[45] Date of Patent: Sep. 30, 1986

[54] 5-AMINO-4-HETEROCYCLYL-1-PHENYL-PYRAZOLES

[75] Inventors: Jörg Stetter; Reinhold Gehring; Markus Lindig, all of Wuppertal; Otto Schallner, Monheim; Ludwig Eue, Leverkusen; Robert R. Schmidt, Bergisch-Gladbach; Hans-Joachim Santel, Cologne; Klaus Lürssen, Bergisch-Gladbach, all of Fed. Rep. of Germany

[73] Assignee: Bayer Aktiengesellschaft, Leverkusen, Fed. Rep. of Germany

[21] Appl. No.: 741,325

[22] Filed: Jun. 4, 1985

[30] Foreign Application Priority Data

Jun. 22, 1984 [DE] Fed. Rep. of Germany ....... 3423101

[51] Int. Cl.[4] ................... A01N 43/56; A01N 43/653; C07D 403/04
[52] U.S. Cl. ......................................... 71/92; 71/90; 71/73; 71/74; 71/76; 71/78; 544/65; 544/182; 544/212; 544/238; 544/333; 544/405; 546/279; 548/125; 548/131; 548/134; 548/137; 548/143; 548/146; 548/202; 548/214; 548/235; 548/237; 548/240; 548/247; 548/255; 548/262; 548/336; 548/348; 548/362; 548/374
[58] Field of Search ................. 544/65, 182, 212, 238, 544/333, 405; 546/279; 548/125, 131, 134, 137, 143, 146, 202, 214, 235, 237, 240, 247, 255, 262, 336, 348, 362, 374; 71/90, 92

[56] References Cited

FOREIGN PATENT DOCUMENTS 0087388 8/1983 European Pat. Off. .
3129429 2/1983 Fed. Rep. of Germany .

OTHER PUBLICATIONS

Okamoto et al, Chemical Abstracts, vol. 100 (1984) 6475p.
Kalk et al, Chemical Abstracts, vol. 83 (1975) 178597b.
Kreutzberger et al, Chemical Abstracts, vol. 93 (1980) 186284u.
Korbonits et al, Chemical Abstracts, vol. 97 (1982) 23676s.
Yamasa Shoyu Co., Chemical Abstracts, vol. 99 (1983) 122839v.
Taylor et al, Chemical Abstracts, vol. 56 (1962) 14287a.
Chandramohan et al, Chemical Abstracts, vol. 78 (1973) 4166s.
Pandit et al, Chemical Abstracts, vol. 79 (1973) 115526z.
Jayanth et al, Chemical Abstracts, vol. 80 (1974) 108415e.
Taylor et al, J. Org. Chem., vol. 26 (1961) pp. 4967-4974.
Chandramohan et al, Indian J. Chem., vol. 10, No. 6 (1972) pp. 573-576.
Pandit et al, Indian J. Chem., vol. 11, No. 6 (1973) pp. 532-537.
Jayanth et al, Indian J. Chem., vol. 11, No. 11 (1973) pp. 1112-1114.
Kreutzberger et al, Chem.-Ztg., vol. 104, No. 5 (1980) pp. 175-176.
Korbonits et al, J. Chem. Soc., Perkin Trans. I, (1982) pp. 759-766.
Okamoto et al, Chem. Pharm. Bull., vol. 31, No. 6 (1983) pp. 2114-2119.

Primary Examiner—Richard L. Raymond
Attorney, Agent, or Firm—Sprung Horn Kramer & Woods

[57] ABSTRACT

5-Amino-4-heterocyclyl-1-phenylpyrazoles of the formula

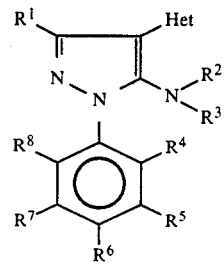

in which
$R^1$ represents hydrogen or alkyl,
$R^2$ represents hydrogen or a radical

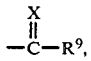

$R^3$ represents hydrogen,

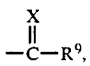

alkyl, alkenyl or alkinyl,
$R^4$, $R^5$, $R^6$, $R^7$ and $R^8$ independently of one another represent hydrogen, cyano, nitro, halogen, alkyl, alkoxy, alkoxycarbonyl, halogenoalkyl, halogenoalkoxy or a radical $-S(O)_n-R^{10}$,
$R^9$ represents hydrogen, alkyl, alkenyl, alkinyl, halogenoalkyl, alkoxyalkyl, alkylthioalkyl, optionally substituted cycloalkyl, optionally substituted aryl, alkoxy, alkylthio, optionally substituted aryloxy or aryloxyalkyl, optionally substituted arylthio, alkylamino, dialkylamino or optionally substituted arylamino,
$R^{10}$ represents alkyl, halogenoalkyl, amino, alkylamino or dialkylamino,
X represents oxygen or sulphur,
n represents the number 0, 1 or 2 and
Het represents a saturated or unsaturated optionally substituted heterocyclic radical,
exhibit herbicidal and plant growth-regulating activity.

12 Claims, No Drawings

5-AMINO-4-HETEROCYCLYL-1-PHENYL-PYRAZOLES

The invention relates to new 5-amino-4-heterocyclyl-1-phenylpyrazoles, several processes for their preparation and their use as herbicides and plate growth regulators.

It is already known that certain 5-amino-1-phenyl-pyrazoles, such as, for example, 5-amino-4-ethoxy-carbonyl-1-(2,4,6-trichlorophenyl)-pyrazole, have herbicidal properties (compare, for example, DE-OS (German Published Specification) No. 3,129,429).

However, the activity of these compounds which are already known is not always completely satisfactory in all fields of application, especially when low amounts and concentrations are applied.

New 5-amino-4-heterocyclyl-1-phenylpyrazoles of the general formula (I)

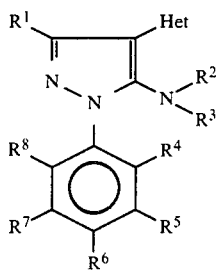

in which
$R^1$ represents hydrogen or alkyl,
$R^2$ represents hydrogen or a radical

$R^3$ independently of $R^2$ represents the same radicals as $R_2$, and additionally represents alkyl, alkenyl or alkinyl, $R^4$, $R^5$, $R^6$, $R^7$ and $R^8$ independently of one another represent hydrogen, cyano, nitro, halogen, alkyl, alkoxy, alkoxycarbonyl, halogenoalkyl, halogenoalkoxy or a radical —S(O)$_n$—$R^{10}$,
$R^9$ represents hydrogen, alkyl, alkenyl, alkinyl, halogenalkyl, alkoxyalkyl, alkylthioalkyl, optionally substituted cycloalkyl, optionally substituted aryl, alkoxy, alkylthio, optionally substituted aryloxy or aryloxyalkyl, optionally substituted arylthio, alkylamino, dialkylamino or optionally substituted arylamino,
$R^{10}$ represents alkyl, halogenoalkyl, amino, alkylamino or dialkylamino,
X represents oxygen or sulphur,
n represents the number 0, 1 or 2 and
Het represents a saturated or unsaturated optionally substituted heterocyclic radical,
have now been found.

It has furthermore been found that the new 5-amino-4-heterocyclyl-1-phenyl-pyrazoles of the general formula (I) are obtained by a process in which (a) phenylhydrazines of the formula (II)

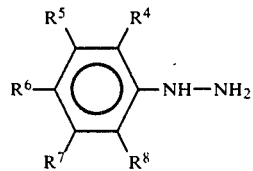

in which
$R^4$, $R^5$, $R^6$, $R^7$ $R^8$ have the abovementioned meaning,
and acrylonitrile derivatives of the formula (III)

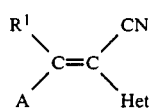

in which
$R^1$ and Het have the abovementioned meaning and
A represents halogen, hydroxyl, alkoxy or dialkylamino,
either are reacted initially in a 1st stage, if appropriate in the presence of a diluent and if appropriate in the presence of a reaction auxiliary, to give the phenylhydrazine derivatives of the formula (IV)

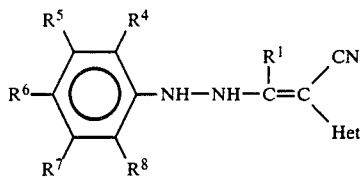

in which
$R^1$, $R^4$, $R^5$, $R^6$, $R^7$ $R^8$ and Het have the abovementioned meaning,
and these are cyclized in a 2nd stage, if appropriate in the presence of a diluent and if appropriate in the presence of an acid catalyst, or are cyclized directly in one reaction step, without isolation of the intermediate of the formula (IV), if appropriate in the presence of a diluent, to give the 5-amino-pyrazoles of the formula (Ia)

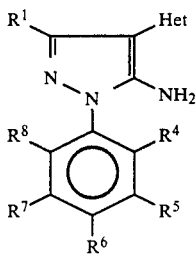

in which
$R^1$, $R^4$, $R^5$, $R^6$, $R^7$, $R^8$ and Het have the abovementioned meaning,
or in which (b) the 5-amino-pyrazoles, obtainable according to process (a), of the formula (Ia)

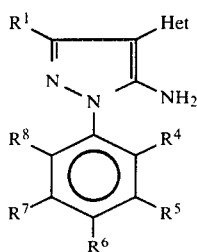

in which
R¹, R⁴, R⁵, R⁶, R⁷, R⁸ and Het have the abovementioned meaning,
are reacted in the generally customary manner with acylating agents or alkylating agents of the formula (V)

$$R^{11}-A' \qquad (V)$$

in which
R¹¹ represents alkyl, alkenyl, alkinyl or $$\text{radical} -\overset{\overset{X}{\|}}{C}-R^9$$

wherein
X and R⁹ have the abovementioned meaning, and
A' represents an electron-attracting leaving group,
or with iso(thio)cyanates of the formula (VI)

$$R^{12}-N=C=X \qquad (VI)$$

in which
R¹² represents alkyl or optionally substituted aryl and X has the abovementioned meaning,
if appropriate in the presence of a diluent and if appropriate in the presence of an acid-binding agent, to give the 5-amino-pyrazoles, alkylated or acylated on the nitrogen, of the formula (Ib)

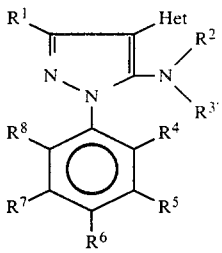

in which
R¹, R², R⁴, R⁵, R⁶, R⁷, R⁸ and Het have the abovementioned meaning and
R³' represents the same radicals as the abovementioned R³, which the exception of the hydrogen radical.

Finally, it has been found that the new 5-amino-4-heterocyclyl-1-phenylpyrazoles of the formula (I) have herbicidal properties, and in particular also selective herbicidal and plate growth-regulating properties.

Surprisingly, the 5-amino-4-heterocyclyl-1-phenylpyrazoles of the formula (I) according to the invention have a considerably better herbicidal activity than the 5-amino-1-phenylpyrazoles known from the prior art, such as, for example, 5-amino-4-ethoxycarbonyl-1-(2,4,6-trichlorophenyl)-pyrazole, which are closely related compounds chemically and from the point of view of their action.

Formula (I) provides a general definition of the 5-amino-4-heterocyclyl-1-phenylpyrazoles according to the invention. Preferred compounds of the formula (I) are those
in which
R¹ represents hydrogen or straight-chain or branched alkyl with 1 to 8 carbon atoms,
R² represents hydrogen or a radical $$-\overset{\overset{}{\|}}{\underset{X}{C}}-R^9,$$

R³ independently of R² represents the same radicals as R², and additionally represents in each case straight-chain or branched alkyl, alkenyl or alkinyl with up to 4 carbon atoms, R⁴, R⁵, R⁶, R⁷ and R⁸ independently of one another represent hydrogen, cyano, nitro, halogen or in each case straight-chain or branched alkyl, alkoxy or alkoxycarbonyl with in each case up to 4 carbon atoms, or represent in each case straight-chain or branched halogenoalkyl or halogenoalkoxy with in each case up to 4 carbon atoms and up to 9 identical or different halogen atoms, or represent a radical $-S(O)_n-R^{10}$,
wherein
R⁹ represents hydrogen or in each case straight-chain or branched alkyl, alkenyl, alkinyl, alkoxyalkyl, alkylthioalkyl, alkoxy, alkylthio, alkylamino, dialkylamino or halogenoalkyl with in each case up to 4 carbon atoms in the individual alkyl parts and, in the case of halogenoalkyl, with up to 9 identical or different halogen atoms, or represents cycloalkyl which has 3 to 7 carbon atoms and is optionally monosubstituted or polysubstituted by identical or different substituents from the group comprising halogen, lower alkyl and lower halogenoalkyl, or represents phenyl, phenoxy, phenoxyalkyl, phenylthio or phenylamino, in each case optionally monosubstituted or polysubstituted by identical or different substituents, possible substituents on the phenyl by halogen, lower alkyl, lower alkoxy and lower halogenoalkyl;
R¹⁰ represents amino or in each case straight-chain or branched alkyl, alkylamino, dialkylamino or halogenoalkyl with in each case up to 4 carbon atoms in the individual alkyl parts, and, in the case of the halogenoalkyl, with up to 9 identical or different halogen atoms,
X represents oxygen or sulphur,
n represents the number 0, 1 or 2 and
Het represents a saturated or unsaturated, five-membered or six-membered heterocyclic radical which is optionally monosubstituted or polysubstituted by identical or different substituents and which contains one to three identical or different heteroatoms from the group comprising nitrogen, oxygen and sulphur and can be linked via a carbon or a nitrogen atom, possible substituents being: halogen, nitro and in each case straight-chain or branched alkyl, alkoxy, alkylthio and halogenoalkyl with in each up to 4 carbon atoms and, where appropriate, up to 9 identical or different halogen atoms.

Particularly preferred compounds of the formula (I) are those
in which $R^1$ represents hydrogen, methyl, ethyl, n- or i- propyl or n-, i-, s- or t-butyl, $R^2$ represents hydrogen or a radical

$R^3$ independently of $R^2$ represents the same radicals as $R^2$, and additionally represents methyl, ethyl, n- or i-propyl, n-, i-, s- or t-butyl or allyl or propargyl, $R^4$, $R^5$, $R^6$, $R^7$ and $R^8$ independently of one another represent hydrogen, cyano, nitro, fluorine, chlorine, bromine, iodine, methyl, ethyl, n- or i-propyl or n-, i-, s- or t-butyl or represent methoxy, ethoxy, methoxycarbonyl or ethoxycarbonyl, or represent trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl or pentachloroethyl, or represent trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy or pentachloroethoxy, or represent a radical $-S(O)_n-R^{10}$, wherein $R^9$ represents hydrogen, methyl, ethyl, n- or i-propyl, allyl, propargyl, butenyl, methoxymethyl, ethoxymethyl, methoxyethyl, ethoxyethyl, methylthiomethyl, methoxy, ethoxy, methylthio, ethylthio, methylamino, ethylamino, dimethylamino, diethylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 3-chloropropyl, 2-bromoethyl or heptafluoro-n-propyl, or represents cyclopropyl, cyclopentyl or cyclohexyl, in each case optionally mono-, di-, tri or tetra-substituted by identical or different substituents from the group comprising fluorine, chlorine, bromine, methyl or trifluoromethyl, or represents phenyl, phenoxy, phenoxymethyl, phenylthio or phenylamino, in each case optionally mono-, di- or tri-substituted by identical or different substituents from the group comprising methyl, methoxy, chlorine and trifluoromethyl, $R^{10}$ represents amino, methylamino, ethylamino, dimethylamino, diethylamino, fluorodichloromethyl, methylamino, difluoromethyl, tetrafluoroethyl, trifluorochloroethyl, trifluoromethyl, methyl or ethyl, X represents oxygen or sulphur, n represents the number 0, 1 or 2 and Het represents a heterocyclic radical of the formula

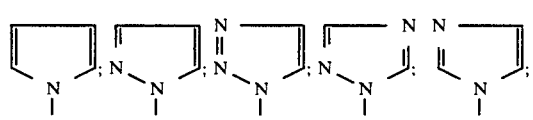

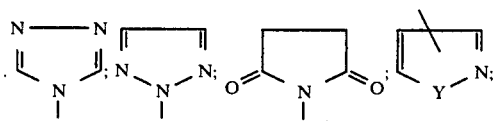

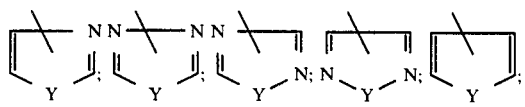

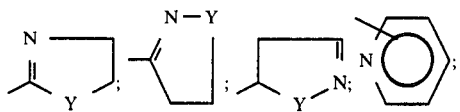

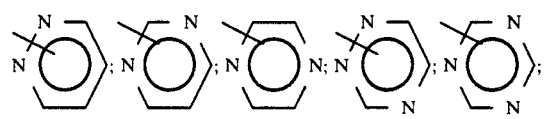

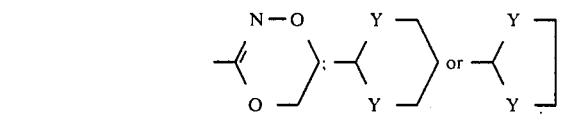

which is optionally mono-, di- or tri-substituted by identical or different substituents from the group comprising fluorine, chlorine, bromine, nitro, methyl, ethyl, n- or i-propyl, methoxy, ethoxy, n- or i-propoxy, methylthio, ethylthio, n- or i-propylthio or trifluoromethyl, wherein Y in each case represents oxygen or sulphur or an N-alkyl radical with up to 4 carbon atoms.

The following 5-amino-4-heterocyclyl-1-phenyl-pyrazoles of the general formula (I) may be mentioned specifically, in addition to the compounds mentioned in the preparation examples:

TABLE 1
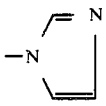
| $R^1$ | $R^2$ | $R^3$ | $R^4$ | $R^5$ | $R^6$ | $R^7$ | $R^8$ | Het |
|---|---|---|---|---|---|---|---|---|
| H | H | H | Cl | H | Cl | H | Cl |  |
| H | H | -C(O)-CH$_3$ | Cl | H | Cl | H | Cl | 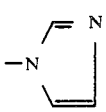 |
| H | H | -C(O)-C$_2$H$_5$ | Cl | H | Cl | H | Cl |  |
| H | H | H | Cl | H | CF$_3$ | H | Cl | 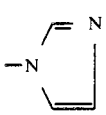 |
| H | H | -C(O)-CH$_3$ | Cl | H | CF$_3$ | H | Cl | 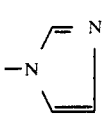 |
| H | H | H | Cl | H | OCF$_3$ | H | H |  |
| H | H | -C(O)-C$_2$H$_5$ | Cl | H | OCF$_3$ | H | H | 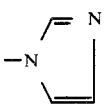 |
| H | H | H | Cl | H | OCF$_3$ | H | Cl | 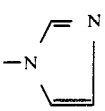 |
| H | H | -C(O)-CH$_3$ | Cl | H | OCF$_3$ | H | Cl |  |
| H | H | -C(O)-C$_2$H$_5$ | Cl | H | OCF$_3$ | H | Cl | 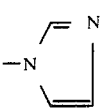 |
| H | H | H | Cl | H | SCF$_3$ | H | Cl | 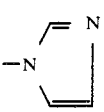 |

TABLE 1-continued
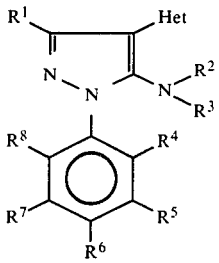
| R¹ | R² | R³ | R⁴ | R⁵ | R⁶ | R⁷ | R⁸ | Het |
|---|---|---|---|---|---|---|---|---|
| H | H | $-\overset{O}{\underset{\|}{C}}-C_2H_5$ | Cl | H | SCF₃ | H | Cl | 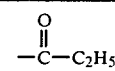 |
| H | H | H | Cl | H | SO₂CF₃ | H | Cl | 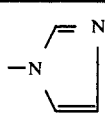 |
| H | H | $-\overset{O}{\underset{\|}{C}}-CH_3$ | Cl | H | SO₂CF₃ | H | Cl | 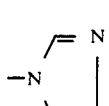 |
| H | H | $-\overset{O}{\underset{\|}{C}}-C_2H_5$ | Cl | H | SO₂CF₃ | H | Cl | 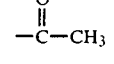 |
| H | H | H | Cl | H | Cl | H | Cl | 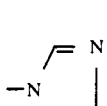 |
| H | H | $-\overset{O}{\underset{\|}{C}}-C_2H_5$ | Cl | H | Cl | H | Cl | 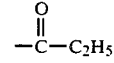 |
| H | H | H | Cl | H | CF₃ | H | Cl | 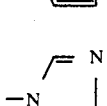 |
| H | H | $-\overset{O}{\underset{\|}{C}}-C_2H_5$ | Cl | H | CF₃ | H | Cl | 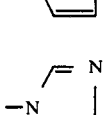 |
| H | H | H | Cl | H | OCF₃ | H | H |  |

TABLE 1-continued $$(I)$$

Structure: Pyrazole with R¹ at 3-position, Het at 4-position, NR²R³ at 5-position, and N1 bearing a phenyl ring substituted with R⁴ (ortho), R⁵ (meta), R⁶ (para), R⁷ (meta), R⁸ (ortho).

| R¹ | R² | R³ | R⁴ | R⁵ | R⁶ | R⁷ | R⁸ | Het |
|---|---|---|---|---|---|---|---|---|
| H | H | —C(=O)—C₂H₅ | Cl | H | OCF₃ | H | H | 1,2,3-triazol-1-yl with NO₂ |
| H | H | H | Cl | H | Cl | H | Cl | 4-NO₂-1,2,4-triazol-1-yl |
| H | H | —C(=O)—C₂H₅ | Cl | H | Cl | H | Cl | 4-NO₂-1,2,4-triazol-1-yl |
| H | H | H | Cl | H | CF₃ | H | Cl | 4-NO₂-1,2,4-triazol-1-yl |
| H | H | —C(=O)—C₂H₅ | Cl | H | CF₃ | H | Cl | 4-NO₂-1,2,4-triazol-1-yl |
| H | H | H | Cl | H | OCF₃ | H | H | 4-NO₂-1,2,4-triazol-1-yl |
| H | H | —C(=O)—C₂H₅ | Cl | H | OCF₃ | H | H | 4-NO₂-1,2,4-triazol-1-yl |
| H | H | H | Cl | H | Cl | H | Cl | 4-Cl-1,2,4-triazol-1-yl |
| H | H | —C(=O)—C₂H₅ | Cl | H | Cl | H | Cl | 4-Cl-1,2,4-triazol-1-yl |

TABLE 1-continued
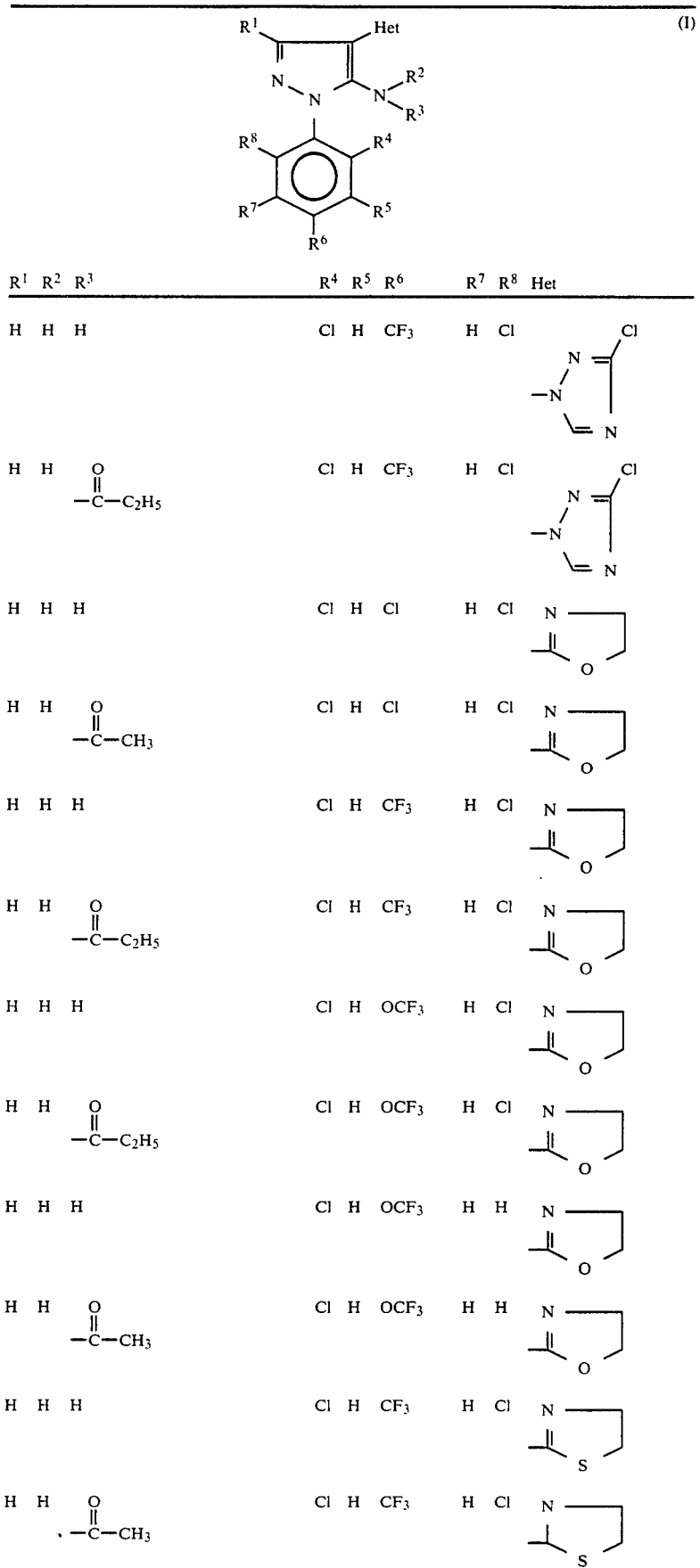

TABLE 1-continued $$\text{(I)}$$

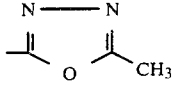

| R¹ | R² | R³ | R⁴ | R⁵ | R⁶ | R⁷ | R⁸ | Het |
|---|---|---|---|---|---|---|---|---|
| H | H | H | Cl | H | Cl | H | Cl |  |
| H | H | $-\overset{O}{\underset{\|}{C}}-C_2H_5$ | Cl | H | Cl | H | Cl | 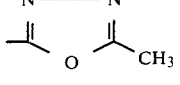 |
| H | H | H | Cl | H | CF₃ | H | Cl | 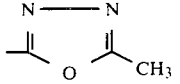 |
| H | H | $-\overset{O}{\underset{\|}{C}}-CH_3$ | Cl | H | CF₃ | H | Cl |  |
| H | H | H | Cl | H | OCF₃ | H | H | 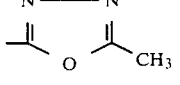 |
| H | H | H | Cl | H | SO₂CF₃ | H | Cl | 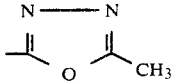 |
| H | H | $-\overset{O}{\underset{\|}{C}}-CH_3$ | Cl | H | SO₂CF₃ | H | Cl | 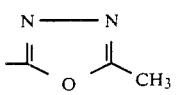 |
| H | H | H | Cl | H | Cl | H | Cl |  |
| H | H | $-\overset{O}{\underset{\|}{C}}-CH_3$ | Cl | H | Cl | H | Cl | 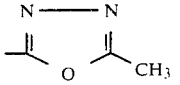 |
| H | H | $-\overset{O}{\underset{\|}{C}}-C_2H_5$ | Cl | H | Cl | H | Cl | 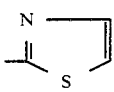 |
| H | H | H | Cl | H | CF₃ | H | Cl |  |
| H | H | $-\overset{O}{\underset{\|}{C}}-C_2H_5$ | Cl | H | CF₃ | H | Cl | 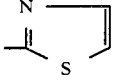 |

TABLE 1-continued

Structure (I):
- Pyrazole ring with R¹ at 3-position, Het at 4-position, N(R²)(R³) at 5-position
- N1 bears a phenyl ring substituted with R⁴ (ortho), R⁵ (meta), R⁶ (para), R⁷ (meta), R⁸ (ortho)

| R¹ | R² | R³ | R⁴ | R⁵ | R⁶ | R⁷ | R⁸ | Het |
|---|---|---|---|---|---|---|---|---|
| H | H | H | Cl | H | OCF₃ | H | H | thiazolyl (N=C-S-C=C) |
| H | H | H | Cl | H | SCF₃ | H | H | thiazolyl |
| H | H | H | Cl | H | SO₂CF₃ | H | H | thiazolyl |
| H | H | CH₃ | Cl | H | Cl | H | Cl | thiazolyl |
| H | H | C₂H₅ | Cl | H | Cl | H | Cl | thiazolyl |
| H | H | —C(=O)—N(CH₃)₂ | Cl | H | Cl | H | Cl | thiazolyl |
| H | H | —C(=O)—OCH₃ | Cl | H | Cl | H | Cl | thiazolyl |
| H | H | —C(=O)—OCH₃ | Cl | H | CF₃ | H | Cl | thiazolyl |
| H | H | —C(=O)—N(CH₃)₂ | Cl | H | CF₃ | H | Cl | thiazolyl |
| H | H | —C(=O)—CH₂O—(2,4-dichlorophenyl) | Cl | H | Cl | H | Cl | thiazolyl |
| H | H | —C(=O)—CH₂O—(2,4-dichlorophenyl) | Cl | H | Cl | H | Cl | 1,2,4-triazolyl |

TABLE 1-continued
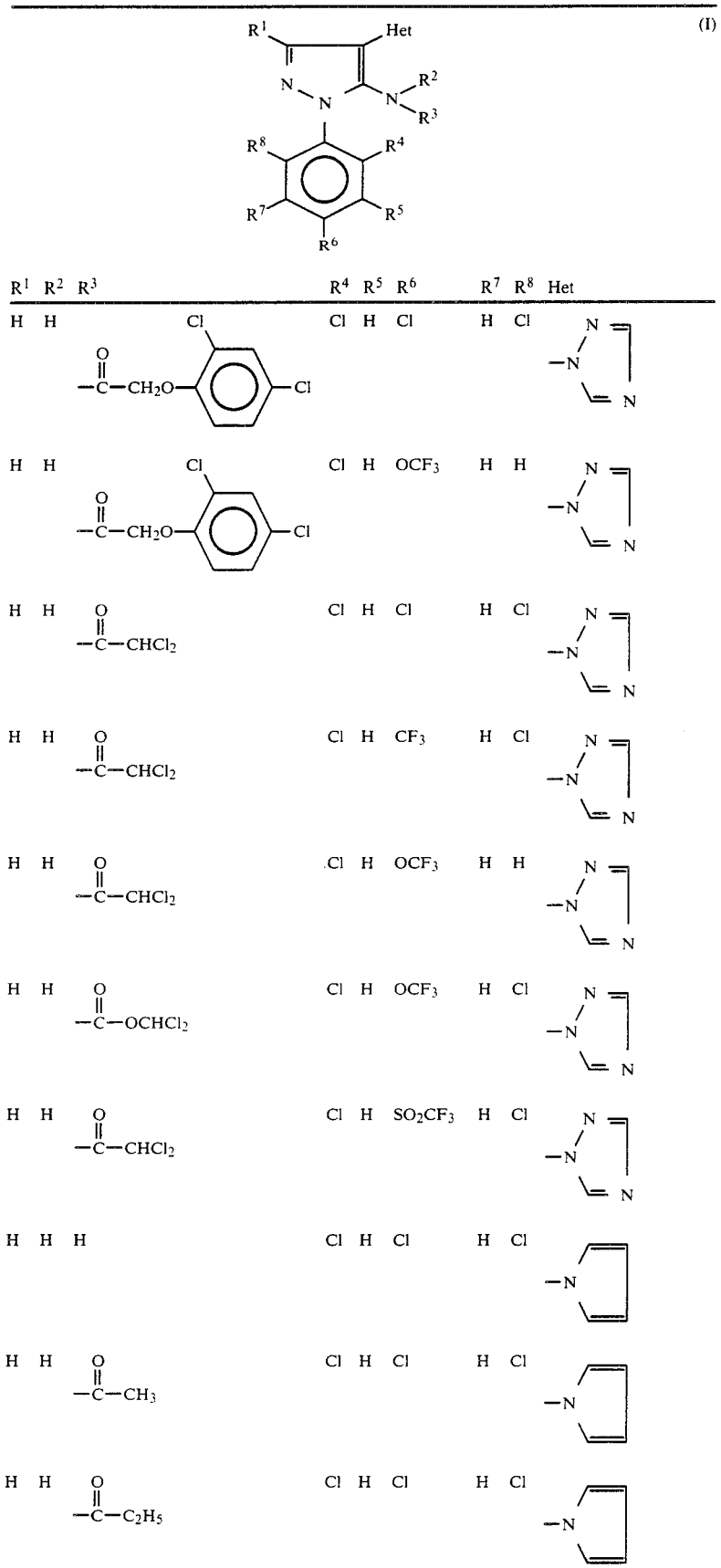

TABLE 1-continued

Structure (I):

Pyrazole core with R¹ at 3-position, Het at 4-position, N(R²)(R³) at 5-position, and N1 bonded to a phenyl ring bearing R⁴ (2'), R⁵ (3'), R⁶ (4'), R⁷ (5'), R⁸ (6').

| R¹ | R² | R³ | R⁴ | R⁵ | R⁶ | R⁷ | R⁸ | Het |
|---|---|---|---|---|---|---|---|---|
| H | H | H | Cl | H | CF₃ | H | Cl | pyrrol-1-yl |
| H | H | —C(O)—CH₃ | Cl | H | CF₃ | H | Cl | pyrrol-1-yl |
| H | H | —C(O)—C₂H₅ | Cl | H | CF₃ | H | Cl | pyrrol-1-yl |
| H | H | H | Cl | H | OCF₃ | H | H | pyrrol-1-yl |
| H | H | H | Cl | H | OCF₃ | H | Cl | pyrrol-1-yl |
| H | H | H | Cl | H | SO₂CF₃ | H | Cl | pyrrol-1-yl |
| H | H | H | Cl | H | Cl | H | Cl | thiazol-2-yl |
| H | H | H | Cl | H | CF₃ | H | Cl | thiazol-2-yl |
| H | H | —C(O)—C₂H₅ | Cl | H | Cl | H | Cl | thiazol-2-yl |
| H | H | —C(O)—C₂H₅ | Cl | H | CF₃ | H | Cl | thiazol-2-yl |
| H | H | H | Cl | H | Cl | H | Cl | oxazol-2-yl |
| H | H | H | Cl | H | CF₃ | H | Cl | oxazol-2-yl |

TABLE 1-continued
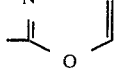
(I)
| R¹ | R² | R³ | R⁴ | R⁵ | R⁶ | R⁷ | R⁸ | Het |
|---|---|---|---|---|---|---|---|---|
| H | H | H | Cl | H | OCF₃ | H | Cl |  |
| H | H | —C(O)—C₂H₅ | Cl | H | CF₃ | H | Cl | 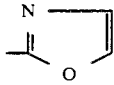 |
| H | H | H | Cl | H | Cl | H | Cl | 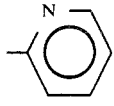 |
| H | H | H | Cl | H | CF₃ | H | Cl | 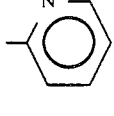 |
| H | H | H | Cl | H | OCF₃ | H | Cl |  |
| H | H | —C(O)—C₂H₅ | Cl | H | Cl | H | Cl | 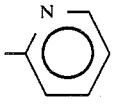 |
| H | H | —C(O)—C₂H₅ | Cl | H | CF₃ | H | Cl |  |
| H | H | H | Cl | H | Cl | H | Cl | 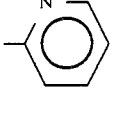 |
| H | H | H | Cl | H | CF₃ | H | Cl | 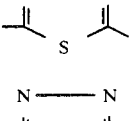 |
| H | H | H | Cl | H | SO₂CH₃ | H | Cl | 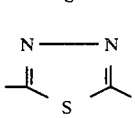 |
| H | H | —C(O)—C₂H₅ | Cl | H | CF₃ | H | Cl | 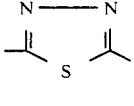 |
| H | H | H | Cl | H | Cl | H | Cl |  |

TABLE 1-continued

Structure (I): Pyrazole with R¹ at position 3, Het at position 4, N(R²)(R³) at position 5, and N1 bonded to a phenyl ring bearing R⁴ (ortho), R⁵ (meta), R⁶ (para), R⁷ (meta), R⁸ (ortho).

| R¹ | R² | R³ | R⁴ | R⁵ | R⁶ | R⁷ | R⁸ | Het |
|---|---|---|---|---|---|---|---|---|
| H | H | H | Cl | H | CF₃ | H | Cl | 3-acetyl-1,2,4-oxadiazol-5-yl (N=N, O, CH₃) |
| H | H | H | Cl | H | Cl | H | Cl | furan-2-yl |
| H | H | H | Cl | H | CF₃ | H | Cl | furan-2-yl |
| H | H | —C(=O)—C₂H₅ | Cl | H | CF₃ | H | Cl | furan-2-yl |
| H | H | —C(=O)—C₂H₅ | Cl | H | Cl | H | Cl | furan-2-yl |
| H | H | H | Cl | H | Cl | H | Cl | 3-methylisoxazol-5-yl |
| H | H | H | Cl | H | CF₃ | H | Cl | 3-methylisoxazol-5-yl |
| H | H | H | Cl | H | OCF₃ | H | Cl | 3-methylisoxazol-5-yl |
| H | H | H | Cl | H | OCF₃ | H | H | 3-methylisoxazol-5-yl |
| H | H | H | Cl | H | Cl | H | Cl | isoxazol-5-yl |
| H | H | H | Cl | H | CF₃ | H | Cl | isoxazol-5-yl |
| H | H | H | Cl | H | SO₂CF₃ | H | Cl | isoxazol-5-yl |

TABLE 1-continued

[Structure (I): Pyrazole with R¹ at 3-position, Het at 4-position, N(R²)(R³) at 5-position, and N1-phenyl bearing R⁴, R⁵, R⁶, R⁷, R⁸ substituents]

| R¹ | R² | R³ | R⁴ | R⁵ | R⁶ | R⁷ | R⁸ | Het |
|---|---|---|---|---|---|---|---|---|
| H | H | H | Cl | H | SCF₃ | H | Cl | isoxazol-3-yl (N–O ring) |
| H | H | H | Cl | H | Cl | H | Cl | 4-nitropyrazol-1-yl |
| H | H | H | Cl | H | CF₃ | H | Cl | 4-nitropyrazol-1-yl |
| H | H | –C(O)–C₂H₅ | Cl | H | CF₃ | H | Cl | 4-nitropyrazol-1-yl |
| H | H | H | Cl | H | Cl | H | Cl | 1,3-dioxolan-2-yl |
| H | H | –C(O)–CH₃ | Cl | H | Cl | H | Cl | 1,3-dioxolan-2-yl |
| H | H | –C(O)–C₂H₅ | Cl | H | Cl | H | Cl | 1,3-dioxolan-2-yl |
| H | H | H | Cl | H | CF₃ | H | Cl | 1,3-dioxolan-2-yl |
| H | H | –C(O)–CH₃ | Cl | H | CF₃ | H | Cl | 1,3-dioxolan-2-yl |
| H | H | –C(O)–C₂H₅ | Cl | H | CF₃ | H | Cl | 1,3-dioxolan-2-yl |

TABLE 1-continued

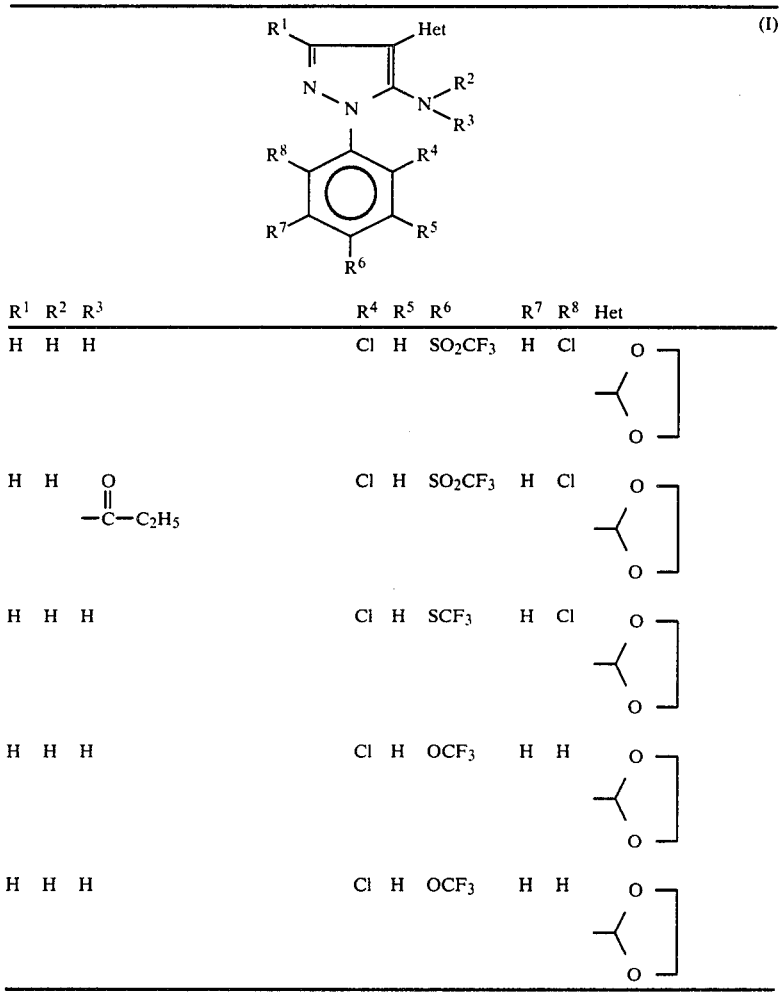

| R¹ | R² | R³ | R⁴ | R⁵ | R⁶ | R⁷ | R⁸ | Het |
|---|---|---|---|---|---|---|---|---|
| H | H | H | Cl | H | $SO_2CF_3$ | H | Cl | (dioxolane) |
| H | H | $-\overset{O}{\underset{\|}{C}}-C_2H_5$ | Cl | H | $SO_2CF_3$ | H | Cl | (dioxolane) |
| H | H | H | Cl | H | $SCF_3$ | H | Cl | (dioxolane) |
| H | H | H | Cl | H | $OCF_3$ | H | H | (dioxolane) |
| H | H | H | Cl | H | $OCF_3$ | H | H | (dioxolane) |

If, for example, 2,6-dichloro-4-trifluoromethyl-phenylhydrazine and 3-dimethylamino-2-(1,2,4-triazol-1-yl)-acrylonitrile hydrochloride are used as starting substances, the course of the reaction in process (a) according to the invention can be represented by the following equation:

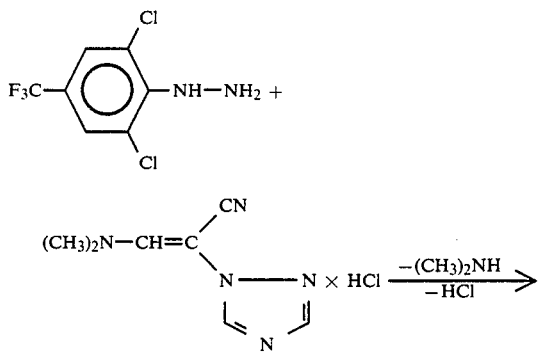

-continued

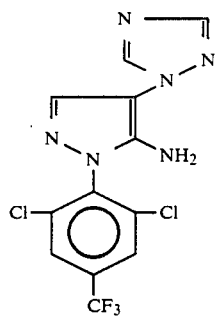

If, for example, 1-(2,6-dichloro-4-trifluoromethyl-phenyl)-5-amino-4-(1,2,4-triazol-1-yl)-pyrazole and propionyl chloride are used as starting substances, the course of the reaction in process (b) according to the invention can be represented by the following equation:

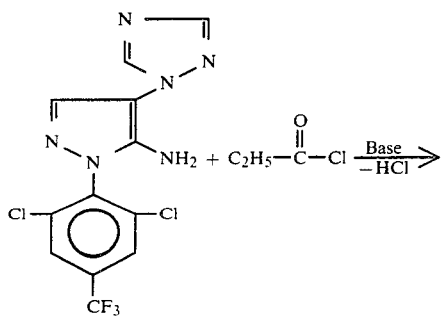

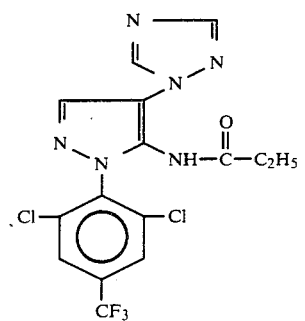

Formula (II) provides a general definition of the phenylhydrazines required as starting substances for carrying out process (a) according to the invention. In this formula (II), $R^4$, $R^5$, $R^6$, $R^7$ and $R^8$ preferably represent those substituents which have already been mentioned as preferred for these radicals in the description of the substances of the formula (I) according to the invention.

The phenylhydrazines of the formula (II) are known in most cases, or they can be prepared by known processes in a simple analogous manner (compare: for example Houben-Weyl "Methoden der organischen Chemie" ("Methods of organic chemistry"), Volume X, 2, page 203, Thieme Verlag Stuttgard 1967), for example by reacting the known anilines of the formula (VII)

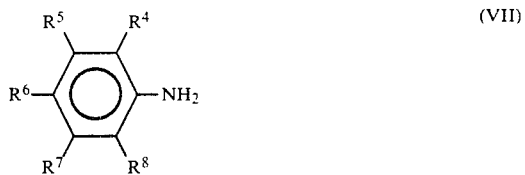

in which
$R^4$, $R^5$, $R^6$, $R^7$ and $R^8$ have the abovementioned meaning,
with sodium nitrite in the presence of an acid, such as, for example, sulphuric acid, and then with tin-II chloride, also in the presence of an acid, such as, for example, hydrochloric acid, at temperatures between $-20°$ C. and $+80°$ C.

Formula (III) provides a general definition of the acrylonitrile derivatives furthermore required as starting substances for carrying out preparation process (a). In this formula (III), $R^1$ and Het preferably represent those radicals which have already been mentioned as preferred for these substituents in the description of the substances of the formula (I) according to the invention. A preferably represents chlorine, bromine, methoxy, ethoxy or dimethylamino.

The acrylonitrile derivatives of the formula (III) are not yet known. They are obtained by a process in which acetonitrile derivatives of the formula (VIII)

in which
Het has the abovementioned meaning,
are reacted either with orthoesters of the formula (IX)

in which
$R^1$ has the abovementioned meaning and
$R^{13}$ represents alkyl, in particular methyl or ethyl,
or with amide-acetals of the formula (X)

in which
$R^1$ has the abovementioned meaning,
$R^{14}$ represents alkyl, in particular methyl or ethyl, and
A" represents dialkylamino, in particular dimethylamino,
if appropriate in the presence of a diluent, such as, for example, toluene, at temperatures between $+80°$ C. and $+200°$ C., or are reacted with esters of the formula (XI)

is in which
$R^1$ has the abovementioned meaning and
$R^{15}$ represents alkyl, in particular methyl or ethyl,
if appropriate in the presence of a diluent, such as, for example, methanol or ethanol, and if appropriate in the presence of a basic catalyst, such as, for example, sodium methylate or ethylate, at temperatures between $0°$ C. and $100°$ C., and the hydroxy compounds thus obtainable, of the formula (IIIa)

in which
$R^1$ and Het have the abovementioned meaning,
are subjected to a substitution reaction in the customary manner using halogenating agents, such as phosphorus pentachloride or thionyl chloride or phosphorus tribromide, at temperatures between $0°$ C. and $+100°$ C.

The anilines of the formula (VII) and the acetonitrile derivatives of the formula (VIII) are known (compare, for example, B. Zh. org. Khim. 18, 463 (1982) s.a.C.A. 96, 181213x; De-OS (German Published Specification) No. 3,129,429; and Ber. dtsch. chem. Ges. 27, 3151 (1894), or they can be prepared by known processes in a simple analogous manner.

The orthoesters of the formula (IX), the amideacetals of the formula (X) and the esters of the formula (XI) are generally known compounds of organic chemistry.

Formula (Ia) provides a general definition of the 5-amino-pyrazoles required as starting substances for carrying out process (b) according to the invention. In this formula (Ia), $R^1$, $R^4$, $R^5$, $R^6R^7$, $R^8$ and Het preferably represent those radicals which have already been mentioned as preferred for these substituents in the description of the substances of the formula (I) which can be used according to the invention.

The 5-aminopyrazoles of the formula (Ia) are compounds according to the invention and can be obtained by preparation process (a).

Formula (V) provides a general definition of the alkylating and acylating agents furthermore required as starting substances for carrying out preparation process (b). In this formula (V), $R^{11}$ preferably represents in each case straight-chain or branched alkyl, alkenyl or alkinyl with up to 4 carbon atoms, or a radical

wherein X and $R^9$ preferably represent those radicals which have already been mentioned as preferred for these radicals in the description of the substances of the formula (I) according to the invention.

A' preferably represents chlorine, bromine or iodine, p-toluenesulphonyloxy, alkoxysulphonyloxy or acyloxy. The alkylating and acylating agents of the formula (V) are generally known compounds of organic chemistry.

FOrmula (VI) provides a general definition of the iso(thio)cyanates which can alternatively be used as starting substances for carrying out preparation process (b). In this formula, X preferably represents oxygen or sulphur and $R^{12}$ preferably represents straight-chain or branched alkyl with up to 4 carbon atoms, or represents phenyl which is optionally mono-, di- or tri-substituted by identical or different substituents, possible substituents being: halogen and in each case straight-chain or branched alkyl, alkoxy and halogenoalkyl with in each case up to 4 carbon atoms and, in the case of the halogenoalkyl, with up to 9 identical or different halogen atoms. $R^{12}$ represents, in particular, methyl, ethyl or phenyl which is optionally mono-, di- or tri-substituted by identical or different substituents from the group comprising fluorine, chlorine, methyl, methoxy and trifluoromethyl. The iso(thio)cyanates of the formula (VI) are likewise generally known compounds of organic chemistry.

Possible diluents for carrying out preparation process (a), both for the 1st and the 2nd reaction stage, are inert organic solvents. Solvents which are preferably used are alcohols, such as methanol, ethanol, propanol, butanol, ethylene glycol and ethylene glycol monomethyl or monoethyl ether.

Possible reaction auxiliaries for carrying out the 1st stage of preparation process (a) are organic or inorganic acids. Acids which are preferably used are sulphuric acid or acetic acid, if appropriate also in the presence of a buffer substance, such as, for example, sodium acetate.

The reaction temperatures can be varied within certain ranges in carrying out the 1st stage of preparation process (a). In general, the reaction is carried out between $-30°$ C. and $+50°$ C., preferably between $-20°$ C. and $+20°$ C.

Possible catalysts for carrying out the 2nd stage of preparation process (a) are all the acids which can usually be employed, such as, for example, sulphuric acid or phosphoric acid.

The reaction temperatures can be varied within a substantial range in carrying out the 2nd stage of preparation process (a), and also in the single-stage reaction procedure. In general, the reaction is carried out between $0°$ C. and $+200°$ C., preferably between $+50°$ C. and $150°$ C.

In carrying out preparation process (a), both in the single-stage and in the two-stage reaction procedure, in general 1.0 to 3.0 moles, preferably 1.0 to 1.5 moles, of acrylonitrile derivative of the formula (III) and, in the case of the two-stage process, if appropriate 1.0 to 10.0 moles of reaction auxiliary in the 1st stage and if appropriate 1.0 to 10.0 moles of acid catalyst in the 2nd stage, are employed per mole of phenylhydrazine of the formula (II).

The reaction products are worked up and isolated by customary processes, for example by removing the organic diluent, precipitating the reaction product in water, and filtering off and drying the product thus obtained.

Possible diluents for carrying out preparation process (b) are likewise inert organic solvents. Solvents which are preferably used are aliphatic or aromatic, optionally halogenated hydrocarbons, such as, for example, benzine, benzene, toluene, xylene, pentane, hexane, heptane, cyclohexane, petroleum ether, ligroin, methylene chloride, chloroform, carbon tetrachloride, chlorobenzene or dichlorobenzene, ethers, such as diethyl ether, diisopropyl ether, dioxane, tetrahydrofuran or ethylene glycol diethyl or dimethyl ether, ketones, such as acetone, butanone, methyl isopropyl ketone or methyl isobutyl ketone, esters, such as ethyl acetate, nitriles, such as acetonitrile or propionitrile, or amides, such as dimethylformamide, dimethylacetamide, N-methylpyrrolidone or hexamethylphosphoric acid triamide. If acylating agents or alkylating agents of the formula (V) or (VI) are used in liquid form, it is also possible to employ these as the diluent in a corresponding excess.

Possible acid-binding agents for carrying out preparation process (b) are all the inorganic and organic bases which can usually be employed. Bases which are preferably used are alkali metal hydrides, hydroxides, amides, carbonates or bicarbonates, such as, for example, sodium hydride, sodium amide, sodium hydroxide, sodium carbonate or sodium bicarbonate, or tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU).

The reaction temperatures can be varied within a substantial range in carrying out preparation process (b). In general, the reaction is carried out between $-20°$ C. and $+150°$ C., preferably between $0°$ C. and $+100°$ C.

For carrying out preparation process (b), in general 1.0 to 20.0 moles, preferably 1.0 to 15.0 moles, of acylating or alkylating agent of the formula (V) or (VI) and, if appropriate, 1.0 to 3.0 moles, preferably 1.0 to 2.0 moles, of acid-binding agent are employed per mole of 5-amino-pyrazole of the formula (Ia). The reaction procedure, working up and isolation of the reaction products of the formula (Ib) are carried out in the generally customary manner.

The active compounds according to the invention can be used as defoliants, desiccants, agents for destroying broad-leaved plants and, especially, as weed-killers.

By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Rutica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be used with particularly good success as agents for selectively combating monocotyledon and dicotyledon weeds, in particular in monocotyledon crops such as corn or wheat.

The active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating compounds can be employed, for example, to inhibit vegetative growth of the plants. Such inhibition of growth is, inter alia, of economic interest in the case of grasses, since it is thereby possible to reduce the frequency of cutting the grass in ornamental gardens, parks and sportsgrounds, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of bending ("lodging") of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soy beans or cereals. Using growth regulators it is also possible, for example, to inhibit the degradation of desired constituents, such as, for example, sugar in sugar beet or sugar cane, before or after harvesting. It is also possible favorably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree ("thinning out") in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for exaple mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkylsulphonates, alkyl-sulphates, arylsulphonates as well as albumin hydrolysis products. As dispersing agents there are suitable: for example, ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

When employed as herbicides the active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethylurea for combating weeds in cereals. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used when employed as a herbicide can vary within a substantial range. It depends essentially on the nature of the desired effect. In general, the amounts used are between 0,01 and 10 kg of active compound per hectare of soil surface, preferably between 0.05 and 5.0 kg per ha.

When used as herbicides and growth regulators, the formulations in general contain between 0.1 and 95 percent by weight of active compound, preferably between 0.5 and 90%.

When used as growthh regulators, the active compounds according to the invention can likewise be present in the formulations as a mixture with other known active compounds, such as fungicides, insecticides, acaricides and herbicides, and also as mixtures with fertilizers and other growth regulators.

The active compounds can thereby likewise be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

When the compounds according to the invention are used as plant growth regulators, the amounts applied can likewise be varied within a substantial range. In general, 0.01 to 50 kg, preferably 0.05 to 10 kg, of active compound are used per hectare of soil surface.

As regards the time of application, the growth regulators are applied within a preferred period of time, the exact definition of which depends on the climatic and vegetative circumstances.

The active compounds according to the invention also exhibit fungicidal and bactericidal properties and, when applied in suitable amounts, can also be used as protective or systemic fungicides, for example against the rice spot disease causative organism (Pyricularia oryzae) or against scab fungi.

The following examples serve to illustrate the invention further.

Preparation Examples:

EXAMPLE 1

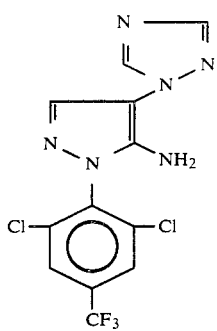
(1)

(Process a)

19 g (0.075 mole) of 2,6-dichloro-4-trifluoromethylphenylhydrazine and 16 g (0.075 mole) of 3-dimethylamino-2-(1,2,4-triazol-1-yl)-acrylonitrile hydrochloride in 200 ml of ethanol are heated at 75° C. to 78° C. for 5 hours, with stirring. For working up, the solvent is distilled off and the residue is triturated with water and dried over clay. 26 g (96% of theory) of 5-amino-1-(2,6-dichloro-4-trifluoromethylphenyl)-4-(1,2,4-triazol-1-yl)-pyrazole of melting point 170°–174° C. are obtained.

Preparation of the starting compound:

(a)

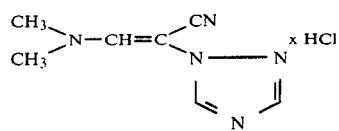

108 g (1 mole) of 1,2,4-triazol-1-yl-acetonitrile and 160 g (1.35 moles) of N,N-dimethylformamide dimethyl acetal are heated under reflux for 4 hours; the methanol formed is distilled off until the internal temperature has risen to 120° C.; the resulting residue is dissolved in 400 ml of ethanol, and 400 ml of a 20% strength ethanolic hydrogen chloride solution are added. The crystalline precipitate is filtered off with suction, rinsed with a little ethanol and dried on clay. 163 g (82% of theory) of 3-dimethylamino-2-(1,2,4-triazol-1-yl)-acrylonitrile hydrochloride of melting point 200°–204° C. are obtained.

(b)

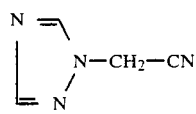

76 g (1 mole) of chloroacetonitrile are added dropwise to a mixture of 69 g (1 mole) of 1,2,4-triazole, 150 g (1.08 moles) of ground potassium carbonate and 500 ml of acetonitrile at 65°–70° C. in the course of 30 minutes, with stirring, and, when the addition has ended, the mixture is stirred at 70° C. for a further 3 hours, the insoluble precipitate is filtered off from the resulting reaction mixture, the filtrate is concentrated in vacuo and the residue is distilled under a high vacuum. 75 g (69% of theory) of 1,2,4-triazol-1-yl-acetonitrile of boiling point 85° C. under 0.01 mbar, which solidifies on cooling and has a melting point of 55° C. to 58° C., are obtained.

EXAMPLE 2

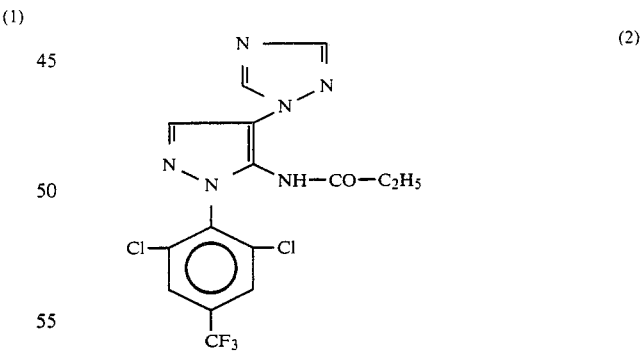
(2)

3.5 g (0.037 mole) of propionyl chloride are added dropwise to a solution of 7.3 g (0.02 mole) of 5-amino-1-(2,6-dichloro-4-trifluoromethylphenyl)-4-(1,2,4-triazol-1-yl)-pyrazole and 2 g (0.025 mole) of pyridine in 60 ml of acetonitrile, with stirring, and, when the addition has ended, the mixture is stirred at room temperature for a further 12 to 15 hours. For working up, the reaction batch is poured into water and extracted with methylene chloride, the organic phase is washed with water and dried over sodium sulphate and the solvent is removed in vacuo. The residue is dissolved in 100 ml of ethanol, 10 ml of aqueous ammonia are added, the mixture is heated to 50° C. for 15 minutes and concentrated in vacuo and the residue is triturated with water and dried on clay. 6.8 g (81% of theory) of 1-(2,6-dichloro-4-trifluoromethyl-phenyl)-5-propionylamino-4-(1,2,4-triazol-1-yl)-pyrazole of melting point 167° C. to 169° C. are obtained.

The following compounds of the general formula (I) are obtained in a corresponding manner and in accordance with the general preparation instructions:

TABLE 2

| Example No. | R¹ | R² | R³ | Phenyl substituents | Het | Melting Point |
|---|---|---|---|---|---|---|
| 3 | H | H | H | 3-Cl, 4-F₃CO | 1,2,4-triazol-1-yl | 116–118° C. |
| 4 | H | H | C₂H₅CO— | 3-Cl, 4-F₃CO | 1,2,4-triazol-1-yl | 108–111° C. |
| 5 | H | H | H | 2,4,6-triCl | 1,2,4-triazol-1-yl | 165–167° C. |
| 6 | H | H | C₂H₅CO— | 2,4,6-triCl | 1,2,4-triazol-1-yl | 205–210° C. |
| 7 | H | H | CH₃O—CH₂—CO— | 2,4,6-triCl | 1,2,4-triazol-1-yl | 140–145° C. |
| 8 | H | H | CH₃CO— | 2,4,6-triCl | 1,2,4-triazol-1-yl | 198° C. |

TABLE 2-continued structure (I):

| Example No. | R¹ | R² | R³ | Aryl (R⁴–R⁸) | Het | Melting Point |
|---|---|---|---|---|---|---|
| 9 | H | H | H | 2,4,5-trichlorophenyl | 4-methylthiazol-2-yl | 141–143° C. |
| 10 | H | H | H | 2,4,5-trichlorophenyl | pyrazol-1-yl | 121–124° C. |
| 11 | H | H | C₂H₅—C(O)— | 2,4,5-trichlorophenyl | 4-methylthiazol-2-yl | — |
| 12 | H | H | C₂H₅—C(O)— | 2,4,5-trichlorophenyl | pyrazol-1-yl | 156–60° C. |
| 13 | H | H | Cl—CH₂—C(O)— | 2,4,5-trichlorophenyl | 1,2,4-triazol-1-yl | 178° C. |
| 14 | H | H | CH₃—C(O)— | 2,4,5-trichlorophenyl | pyrazol-1-yl | 208–210° C. |

TABLE 2-continued

Structure (I):
- Pyrazole with R¹ at 3-position, Het at 4-position, NR²R³ at 5-position, and N1 bearing phenyl substituted with R⁴, R⁵, R⁶, R⁷, R⁸.

| Example No. | R¹ | R² | R³ | R⁵ R⁴ / R⁶ / R⁷ R⁸ (phenyl) | Het | Melting Point |
|---|---|---|---|---|---|---|
| 15 | H | H | (CH₃)₂CH—C(=O)— | 2,4,5-Cl₃ phenyl | 2-methyl-4-thiazolyl (S, N, CH₃) | 183–185° C. |
| 16 | H | H | H | 3-Cl, 4-CF₃ phenyl | 1,2,4-triazol-1-yl | 156–159° C. |
| 17 | H | H | H | 2,3,4-Cl₃ phenyl | 1,2,4-triazol-1-yl | 165° C. |
| 18 | H | H | CH₃—NH—C(=O)— | 2,4,5-Cl₃ phenyl | pyrazol-1-yl | 209–219° C. |
| 19 | H | H | Cl—CH₂—C(=O)— | 2,4,5-Cl₃ phenyl | pyrazol-1-yl | 155–157° C. |
| 20 | H | H | CH₃O—CH₂—C(=O)— | 2,4,5-Cl₃ phenyl | pyrazol-1-yl | 126–128° C. |
| 21 | H | CH₃NHC(=O)— | CH₃—NH—C(=O)— | 2,4,5-Cl₃ phenyl | pyrazol-1-yl | 145–147° C. |

TABLE 2-continued
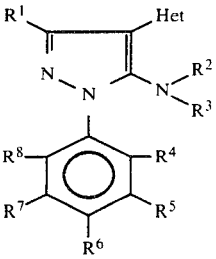
(I)
| Example No. | R¹ | R² | R³ | R⁵ R⁴ / R⁶ / R⁷ R⁸ | Het | Melting Point |
|---|---|---|---|---|---|---|
| 22 | H | H | Cl—CH₂—C(=O)— | 3-Cl, 4-FCF₃ (F₃C-, Cl) | -N-N=CH-N=CH (1,2,4-triazol-1-yl) | 155–158° C. |
| 23 | H | H | (CH₃)₂CH—C(=O)— | 2,3,4-tri-Cl | triazolyl | >230° C. |
| 24 | H | H | C₂H₅—C(=O)— | 3-Cl, 4-CF₃ | triazolyl | 155–159° C. |
| 25 | H | H | C₂H₅—C(=O)— | 2,3,4-tri-Cl | triazolyl | 242–244° C. |
| 26 | H | H | H | 3,5-di-Cl, 4-OCF₃ | triazolyl | 112–115° C. |
| 27 | H | H | H | 3-Cl, 4-Br | triazolyl | 88–93° C. |
| 28 | H | CH₃NH—C(=O)— | CH₃NH—C(=O)— | 2,4,5-tri-Cl | triazolyl | 152–159° C. |

TABLE 2-continued (I)

[Structure: Pyrazole with R¹, Het, NR²R³ substituents and N-phenyl group bearing R⁴, R⁵, R⁶, R⁷, R⁸]

[Phenyl numbering diagram showing R⁴, R⁵, R⁶, R⁷, R⁸ positions]

| Example No. | R¹ | R² | R³ | Phenyl substituents | Het | Melting Point |
|---|---|---|---|---|---|---|
| 29 | H | H | CH₃-C(=O)- | 2,4-Cl₂, 5-OCF₃ | 1,2,4-triazol-1-yl | 188–192° C. |
| 30 | H | H | CH₃-NH-C(=O)- | 2,4,5-Cl₃ | 1,2,4-triazol-1-yl | 210–212° C. |
| 31 | H | H | C₂H₅-C(=O)- | 2,4-Cl₂, 5-OCF₃ | 1,2,4-triazol-1-yl | 138–140° C. |
| 32 | H | H | (CH₃)₂CH-C(=O)- | 2-Cl, 4-Br | 1,2,4-triazol-1-yl | 157–159° C. |
| 33 | H | H | C₂H₅-C(=O)- | 2-Cl, 4-Br | 1,2,4-triazol-1-yl | 150–153° C. |
| 34 | H | H | ClCH₂-C(=O)- | 2,4-Cl₂, 5-CF₃ | 1,2,4-triazol-1-yl | 156–158° C. |
| 35 | H | H | H | 2,4,6-Br₃ | 1,2,4-triazol-1-yl | 179–181° C. |

TABLE 2-continued
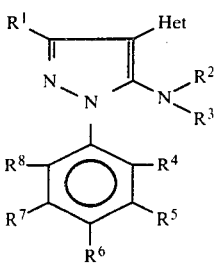
(I)
| Example No. | R¹ | R² | R³ | R⁵ R⁴ / R⁶ \ / \ / R⁷ R⁸ | Het | Melting Point |
|---|---|---|---|---|---|---|
| 36 | H | H | H | 2,4,5-Cl₃-phenyl | $\underset{N}{\overset{N=N}{-N}}$ triazole | 146–148° C. |
| 37 | H | H | (CH₃)₂CH—C(O)— | 2,4,6-Br₃-phenyl | triazole | 92–98° C. |
| 38 | H | H | C₂H₅—C(O)— | 2,4,6-Br₃-phenyl | triazole | 118–120° C. |
| 39 | H | H | C₂H₅—C(O)— | 2,4,5-Cl₃-phenyl | triazole | 178–182° C. |
| 40 | H | H | Cl(CH₂)₃—C(O)— | 2,4,5-Cl₃-phenyl | triazole | 195–200° C. |
| 41 | H | C₂H₅—C(O)— | CH₃— | 2,4,5-Cl₃-phenyl | triazole | 163° C. |

TABLE 2-continued (I)

| Example No. | R¹ | R² | R³ | R⁴ R⁵ R⁶ R⁷ R⁸ (phenyl substitution) | Het | Melting Point |
|---|---|---|---|---|---|---|
| 42 | H | H | $CH_3-$ | 2,5-dichlorophenyl | $-N-N=CH-N=$ (1,2,4-triazol-1-yl) | 150–155° C. |
| 43 | H | $C_2H_5-C(=O)-$ | $CH_2=CH-CH_2-$ | 2,5-dichlorophenyl | 1,2,4-triazol-1-yl | 112° C. |
| 44 | H | H | H | 2,5-dichloro-4-($CF_3SO_2$)phenyl | 1,2,4-triazol-1-yl | 126–131° C. |
| 45 | H | H | $C_2H_5-C(=O)-$ | 2,5-dichloro-4-($CF_3SO_2$)phenyl | 1,2,4-triazol-1-yl | 238° C. |
| 46 | H | H | $C_2H_5-C(=O)-$ | 2,6-dichlorophenyl | 1,2,4-triazol-1-yl | 202–204° C. |
| 47 | H | H | $C_2H_5-C(=O)-$ | 4-nitrophenyl | 1,2,4-triazol-1-yl | 198–100° C. |
| 48 | H | H | H | 3-($CF_3$)phenyl | 1,2,4-triazol-1-yl | 104° C. |

TABLE 2-continued

Structure (I): Pyrazole with R¹ at 3-position, Het at 4-position, NR²R³ at 5-position, and N1-substituted with phenyl ring bearing R⁴ (ortho), R⁵ (meta), R⁶ (para), R⁷ (meta), R⁸ (ortho).

Phenyl substituent pattern shown with R⁴, R⁵, R⁶, R⁷, R⁸ positions.

| Example No. | R¹ | R² | R³ | Phenyl (R⁴–R⁸) | Het | Melting Point |
|---|---|---|---|---|---|---|
| 49 | H | H | H | 2,4,5-trichlorophenyl | thiazol-2-yl (N=C-S ring) | 178–180° C. |
| 50 | H | H | C₂H₅−C(=O)− | 2,4,5-trichlorophenyl | thiazol-2-yl | 124° C. |
| 51 | H | H | H | 2,6-dichlorophenyl | 1,2,4-triazol-1-yl | 156–170° C. |
| 52 | H | H | H | 4-nitrophenyl | 1,2,4-triazol-1-yl | 218–220° C. |
| 53 | H | H | H | phenyl | 1,2,4-triazol-1-yl | 139° C. |
| 54 | H | H | C₂H₅−C(=O)− | phenyl | 1,2,4-triazol-1-yl | 159–161° C. |
| 55 | H | H | C₂H₅−C(=O)− | 2,3,4-trichlorophenyl | 2,5-dimethylpyrrol-1-yl | 195° C. |

TABLE 2-continued

Structure (I): Pyrazole with R¹ at 3-position, Het at 4-position, NR²R³ at 5-position, and N1 substituted with phenyl ring bearing R⁴, R⁵, R⁶, R⁷, R⁸.

Phenyl substitution pattern reference:
- R⁴: position 2
- R⁵: position 3
- R⁶: position 4
- R⁷: position 5
- R⁸: position 6

| Example No. | R¹ | R² | R³ | Phenyl substituents | Het | Melting Point |
|---|---|---|---|---|---|---|
| 56 | H | H | $C_2H_5-C(=O)-$ | 2,3,6-trichlorophenyl | succinimido (pyrrolidine-2,5-dione-N-yl) | 89–90° C. |
| 57 | H | H | $CH_2=CH-CH_2-$ | 2,4,6-trichlorophenyl | 1,2,4-triazol-1-yl | |
| 58 | H | H | H | 2-CF₃, 3,5-dinitrophenyl | 1,2,4-triazol-1-yl | 178–182° C. |
| 59 | H | H | $C_2H_5-C(=O)-$ | 3-CF₃-phenyl | 1,2,4-triazol-1-yl | 123–124° C. |
| 60 | H | H | $Cl_2CH-C(=O)-$ | 2,4,6-trichlorophenyl | 1,2,4-triazol-1-yl | |
| 61 | H | H | $C_2H_5-CO-$ | 2-CF₃, 4,5-dichlorophenyl | 1,2,4-triazol-4-yl | 188°–190° C. |

TABLE 2-continued (I)

| Example No. | R¹ | R² | R³ | R⁵ R⁴<br>R⁶<br>R⁷ R⁸ | Het | Melting Point |
|---|---|---|---|---|---|---|
| 62 | H | H | H | 2,6-Cl, 4-Br phenyl | 1,2,4-triazol-1-yl | 170° C. |
| 63 | H | C₂H₅—CO | H | 2,6-Cl, 4-Br phenyl | 1,2,4-triazol-1-yl | 193° C. |
| 64 | H | H | CH₂=CH—CH₂— | 2,4,6-trichlorophenyl | 1,2,4-triazol-1-yl | 100°–105° C. |
| 65 | H | H | H | 3,5-Br, 4-CH₃OOC phenyl | 1,2,4-triazol-1-yl | Oil |
| 66 | H | H | (CH₃)₂C=CH—CO— | 2,4,6-trichlorophenyl | 1,2,4-triazol-1-yl | 196°–200° C. |
| 67 | H | H | H | 3,5-Cl, 4-CN phenyl | 1,2,4-triazol-1-yl | 235° C. |

TABLE 2-continued

Structure (I): pyrazole with R¹ at 3-position, Het at 4-position, N(R²)(R³) at 5-position, and N1-substituted phenyl bearing R⁴, R⁵, R⁶, R⁷, R⁸.

| Example No. | R¹ | R² | R³ | Phenyl (R⁴–R⁸) | Het | Melting Point |
|---|---|---|---|---|---|---|
| 68 | H | CH₃—CH=CH—CO— | CH₃—CH=CH—CO— | 2,4,6-trichlorophenyl | 1,2,4-triazol-1-yl | Oil |
| 69 | H | H | H | 3-chloro-4-(methoxycarbonyl)phenyl | 1,2,4-triazol-1-yl | 165°–170° C. |
| 70 | H | H | C₂H₅CO— | 3,5-dibromo-4-(methoxycarbonyl)phenyl | 1,2,4-triazol-1-yl | 95°–98° C. |
| 71 | H | H | H | 2,3-dichloro-5-(trifluoromethyl)phenyl | 1,2,4-triazol-1-yl | 60°–65° C. |
| 72 | H | H | ClCH₂—CO— | 2,3-dichloro-5-(trifluoromethyl)phenyl | 1,2,4-triazol-1-yl | 116°–118° C. |
| 73 | H | H | C₂H₅CO— | 3-chloro-4-(methoxycarbonyl)phenyl | 1,2,4-triazol-1-yl | 135–138° C. |
| 74 | H | H | C₂H₅CO— | 2,5-dibromo-3-(trifluoromethyl)phenyl | 1,2,4-triazol-1-yl | 174° C. |

TABLE 2-continued

Structure (I):
Pyrazole with R¹ at position 3, Het at position 4, NR²R³ at position 5, N1 bearing phenyl substituted with R⁴, R⁵, R⁶, R⁷, R⁸.

| Example No. | R¹ | R² | R³ | Phenyl (R⁴–R⁸) | Het | Melting Point |
|---|---|---|---|---|---|---|
| 75 | H | H | H | 4-CF₃-phenyl | 1,2,3-triazol-2-yl | 175°–177° C. |
| 76 | H | H | H | 4-Cl-2-F-phenyl | 1,2,3-triazol-2-yl | 140° C.–142° C. |
| 77 | H | H | H | 3,5-dichloro-4-(CH₃OOC)-phenyl | 1,2,3-triazol-2-yl | 148° C. |
| 78 | H | H | H | 3-Br-4-(CH₃OOC)-phenyl | 1,2,3-triazol-2-yl | 140°–142° C. |
| 79 | H | H | C₂H₅CO— | 4-CF₃-phenyl | 1,2,3-triazol-2-yl | 155°–158° C. |
| 80 | H | H | ClCH₂—CO— | 4-Cl-2-F-phenyl | 1,2,3-triazol-2-yl | 145° C. |
| 81 | H | H | C₂H₅CO— | 4-Cl-2-F-phenyl | 1,2,3-triazol-2-yl | 175° C. |
| 82 | H | H | C₂H₅CO— | 3,5-dichloro-4-(CH₃OOC)-phenyl | 1,2,3-triazol-2-yl | 188° C. |

TABLE 2-continued

Structure (I):
Pyrazole with R¹ at 3-position, Het at 4-position, N(R²)(R³) at 5-position, and N-phenyl substituted with R⁴–R⁸.

| Example No. | R¹ | R² | R³ | Phenyl substituents | Het | Melting Point |
|---|---|---|---|---|---|---|
| 83 | H | H | F₃C—CO— | 2-Cl, 4-CF₃, 6-Cl | 1,2,4-triazol-1-yl | 215°–218° C. |
| 84 | H | H | H | 2-Cl, 4-F | 1,2,4-triazol-1-yl | 130° C.–134° C. |
| 85 | H | H | C₂H₅—CO— | 2-Cl, 4-F | 1,2,4-triazol-1-yl | 140°–142° C. |
| 86 | H | H | H | 2-Br, 4-CF₃, 6-Br | 1,2,4-triazol-1-yl | 166° C. |
| 87 | H | H | C₂H₅—CO— | 2-Br, 4-(CH₃COO) | 1,2,4-triazol-1-yl | 110°–112° C. |

USE EXAMPLES

The compound shown below was used as the comparison substance in the use examples which follow:

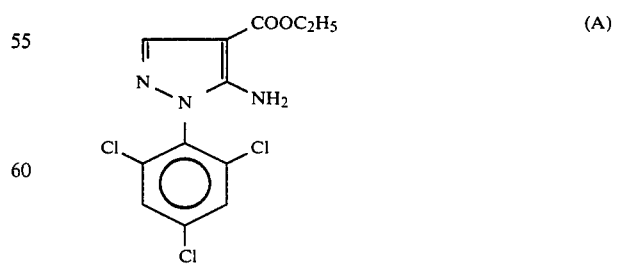

(A)

5-Amino-4-ethoxycarbonyl-1-(2,4,6-trichlorophenyl)-pyrazole (known from DE-OS (German Published Specification) No. 3,129,429).

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a clearly superior activity to the prior art, coupled with a comparable selectivity towards crop plants, is shown, for example, by the compounds according to the following preparation Examples: 1 and 2.

EXAMPLE B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, a clearly superior activity to the prior art, coupled with a comparable selectivity towards crop plants is shown, for example, by the compounds according to the following preparation Examples: 1 and 2.

EXAMPLE C

Inhibition of growth of barley
Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Barely plants are grown in a greenhouse to the 2-leaf stage. In this stage, the plants are sprayed with the preparations of active compound until dripping wet. After 3 weeks, the additional growth is measured on all plants and the inhibition of growth in percent of the additional growth of the control plants is calculated. 100% inhibition of growth means that growth has stopped and 0% denotes a growth corresponding to that of the control plants.

In this test, a clear activity in comparison with the untreated control is shown, for example, by the compound according to the preparation Example 5.

EXAMPLE D

Defoliation and desiccation of the leaves of cotton
Solvent: 30 parts by weight of dimethylformamide
Emulsifier: 1 part by weight of polyoxyethylene sorbitana monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 1 week, the shedding of leaves and the desiccation of the leaves are rated, in comparison with the control plants.

In this test, a clear activity in comparison with the untreated control is shown, for example, by the compound according to preparation Example 6.

It will be understood that the specification and examples are illustrative but not limitative of the present invention and that other embodiments within the spirit and scope of the invention will suggest themselves to those skilled in the art.

We claim:

1. A 5-amino-4-heterocyclyl-1-phenylpyrazole of the formula

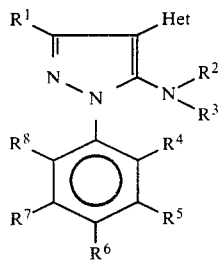

in which
R$^1$ represents hydrogen or straight-chain or branched alkyl with 1 to 8 carbon atoms,
R$^2$ represents hydrogen or a radical

R$^3$ represents hydrogen,

or alkyl, alkenyl or alkinyl with up to 4 carbon atoms,
R$^4$, R$^5$, R$^6$, R$^7$ and R$^8$ independently of one another represent hydrogen, cyano, nitro, halogen or alkyl, alkoxy or alkoxycarbonyl with in each case up to 4 carbon atoms, or represent halogenoalkyl or halogenoalkoxy with in each case up to 4 carbon atoms and up to 9 halogen atoms, or represent a radical —S(O)$_n$—R$^{10}$, R$^9$ represents hydrogen or alkyl, alkenyl, alkinyl, alkoxyalkyl, alkylthioalkyl, alkoxy, alkylthio, alkylamino, dialkylamino or halogenoalkyl with in each case up to 4 carbon atoms in the individual alkyl parts and, in the case of halogenoalkyl, with up to 9 halogen atoms, or represents cycloalkyl which has 3 to 7 carbon atoms and is optionally substituted by halogen, lower alkyl and lower halogenoalkyl, or represents phenyl, phenoxy, phenoxyalkyl, phenylthio or phenylamino, in each case optionally substituted on the phenyl by halogen, lower alkyl, lower alkoxy and lower halogenoalkyl;

R$^{10}$ represents amino or alkyl, alkylamino, dialkylamino or halogenoalkyl with in each case up to 4 carbon atoms in the individual alkyl parts and, in the case of halogenoalkyl, with up to 9 halogen atoms, X represents oxygen or sulphur, n represents the number 0, 1 or 2, Het represents a heterocyclic radical of the formula

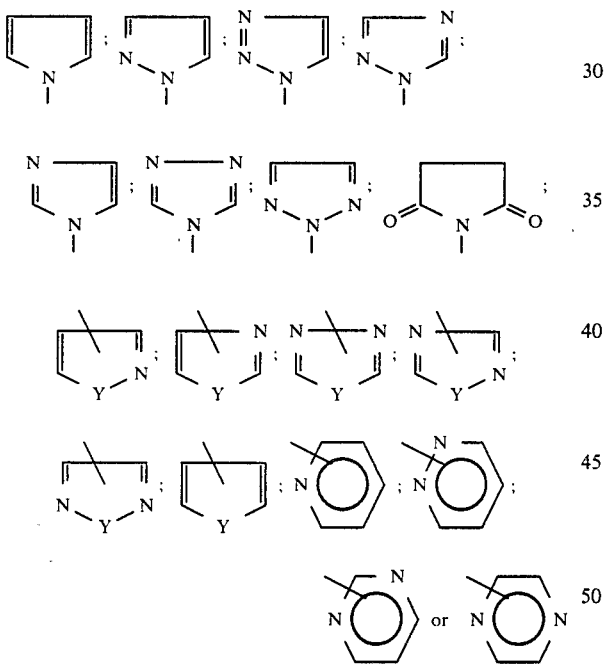

which is optionally substituted by halogen, nitro, or alkyl, alkoxy, alkylthio and/or halogenoalkyl with in each case up to 4 carbon atoms and, where appropriate, up to 9 halogen atoms, and Y in each case represents oxygen, sulphur or an N-alkyl radical with up to 4 carbon atoms.

2. A compound according to claim 1, in which

R$^1$ represents hydrogen, methyl, ethyl, n- or i-propyl or n-, i-, s- or t-butyl, R$^3$ represents hydrogen, $$-\overset{X}{\underset{\|}{C}}-R^9,$$

methyl, ethyl, n- or i-propyl, n-, i-, s- or t-butyl or allyl or proparyl,

R$^4$, R$^5$, R$^6$, R$^7$ and R$^8$ independently of one another represent hydrogen, cyano, nitro, fluorine, chlorine, bromine, iodine, methyl, ethyl, n- or i-propyl, or n-, i-, s- or t-butyl or represent methoxy, ethoxy, methoxycarbonyl or ethoxycarbonyl, or represent trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl or pentachloroethyl, or represent trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy or pentachloroethoxy, or represent a radical —S(O)$_n$—R$^{10}$, R$^9$ represents hydrogen, methyl, ethyl, n- or i-propyl, allyl, propargyl, butenyl, methoxymethyl, ethoxymethyl, methoxyethyl, ethoxyethyl, methylthiomethyl, methoxy, ethoxy, methylthio, ethylthio, methylamino, ethylamino, dimethylamino, diethylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 3-chloropropyl, 2-bromoethyl or heptafluoro-n-propyl, or represents cyclopropyl, cyclopentyl or cyclohexyl, in each case optionally mono-, di-, tri or tetra-substituted by fluorine, chlorine, bromine, methyl and/or trifluoromethyl, or represents phenyl, phenoxy, phenoxymethyl, phenylthio or phenylamino, in each case optionally mono-, di- or trisubstituted by methyl, methoxy, chlorine and/or trifluoromethyl, and R$^{10}$ represents amino, methylamino, ethylamino, dimethylamino, diethylamino, fluorodichloromethyl, difluoromethyl, tetrafluoroethyl, trifluorochloroethyl, trifluoromethyl, methyl or ethyl.

3. A compound according to claim 1, wherein such compound is 5-amino-1-(2,6-dichloro-4-trifluoromethylphenyl)-4-(1,2,4-triazol-1-yl)-pyrazole of the formula

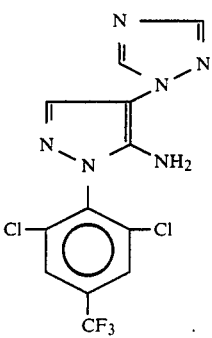

4. A compound according to claim 1, wherein such compound is 1-(2,6-dichloro-4-trifluoromethyl-phenyl)-5-propionylamino-4-(1,2,4-triazol-1-yl)-pyrazole of the formula

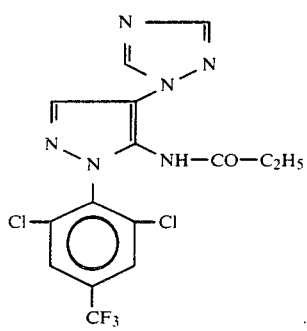

5. A compound according to claim 1, wherein such compound is 1-(2,6-dichloro-4-trifluoromethoxyphenyl)-5-propionylamino-4-(1,2,4-triazol-1-yl)-pyrazole of the formula

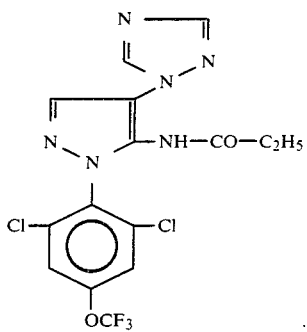

6. A compound according to claim 1, wherein such compounds is 5-amino-4-(1,2,3-triazol-1-yl)-1-(2,4,6-trichlorophenyl)-pyrazole of the formula

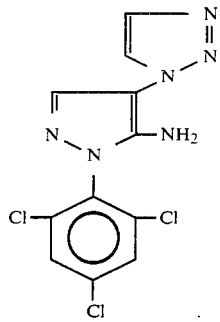

7. A compound according to claim 1, wherein such compound is 5-amino-1-(2,6-dichloro-4-trifluoromethylsulphonylphenyl)-4-(1,2,4-triazol-1-yl)-pyrazole of the formula

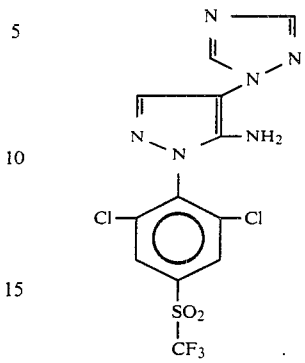

8. A herbicidal or plant growth-regulating composition comprising a herbicidally or plant growth-regulating effective amount of a compound according to claim 1 in admixture with a diluent.

9. A method of combating undesired vegetation which comprises applying to such vegetation or to a locus from which it is desired to exclude such vegetation a herbicidally effective amount of a compound according to claim 1.

10. The method according to claim 9, wherein such compound is
5-amino-1-(2,6-dichloro-4-trifluoromethyl-phenyl)-4-(1,2,4-triazol-1-yl)-pyrazole,
1-(2,6-dichloro-4-trifluoromethyl-phenyl)-5-propionylamino-4-(1,2,4-triazol-1-yl)-pyrazole,
1-(2,6-dichloro-4-trifluoromethoxy-phenyl)-5-propionylamino-4-(1,2,4-triazol-1-yl)-pyrazole,
5-amino-4-(1,2,3-triazol-1-yl)-1-(2,4,6-trichlorophenyl)-pyrazole or
5-amino-1-(2,6-dichloro-4-trifluoromethyl-sulphonylphenyl)-4-(1,2,4-triazol-1-yl)-pyrazole.

11. A method of regulating the growth of plants which comprises applying to such plants or to a locus in which such plants are grown a plant growth-regulating effective amount of a compound according to claim 1.

12. The method according to claim 11, wherein such compound is
5-amino-1-(2,6-dichloro-4-trifluoromethyl-phenyl)-4-(1,2,4-triazol-1-yl)-pyrazole,
1-(2,6-dichloro-4-trifluoromethyl-phenyl)-5-propionylamino-4-(1,2,4-triazol-1-yl)-pyrazole,
1-(2,6-dichloro-4-trifluoromethoxy-phenyl)-5-propionylamino-4-(1,2,4-triazol-1-yl)-pyrazole,
5-amino-4-(1,2,3-triazol-1-yl)-1-(2,4,6-trichlorophenyl)-pyrazole or
5-amino-1-(2,6-dichloro-4-trifluoromethyl-sulphonylphenyl)-4-(1,2,4-triazol-1-yl)-pyrazole.

* * * * *